(12) United States Patent
Pfeifer et al.

(10) Patent No.: US 8,471,223 B2
(45) Date of Patent: Jun. 25, 2013

(54) APPARATUS AND METHOD FOR SAMPLE PREPARATION

(75) Inventors: Thomas Pfeifer, Zschopau (DE); Heinz Plank, Wr. Neudorf (AT)

(73) Assignee: Leica Mikrosysteme GmbH, Vienna (AT)

( * ) Notice: Subject to any disclaimer, the term of this patent is extended or adjusted under 35 U.S.C. 154(b) by 17 days.

(21) Appl. No.: 13/368,414

(22) Filed: Feb. 8, 2012

(65) Prior Publication Data

US 2012/0199552 A1    Aug. 9, 2012

(30) Foreign Application Priority Data

Feb. 9, 2011    (AT) .................................. A 168/2011

(51) Int. Cl.
*G01N 23/00*    (2006.01)
(52) U.S. Cl.
USPC ...................... 250/491.1; 250/492.22; 216/66
(58) Field of Classification Search
USPC ....................................................... 250/491.1
See application file for complete search history.

(56) References Cited

U.S. PATENT DOCUMENTS

| 3,993,909 A | 11/1976 | Drews et al. |
| 4,663,009 A * | 5/1987 | Bloomquist et al. ........ 204/192.2 |
| 6,238,531 B1 * | 5/2001 | Pinarbasi ................. 204/298.04 |
| 2010/0025577 A1 | 2/2010 | Grünewald et al. |

* cited by examiner

*Primary Examiner* — Phillip A Johnston
(74) *Attorney, Agent, or Firm* — Hodgson Russ LLP

(57) ABSTRACT

A sample stage for processing a sample in an ion beam etching apparatus has positioning arrangements each having a receiving apparatus and a mask, a sample being mountable in the receiving apparatus with reference to an ion beam and positionable relative to the mask. The sample stage includes a mechanism that enables a switchover between respective positioning arrangements so a selected positioning arrangement is respectively orientable toward the ion beam. The sample in the selected positioning arrangement is exposed to the ion beam while the remaining positioning arrangements face away from the ion beam. The positioning arrangements are arranged in one common vessel. A method for sequential preparation of at least two samples in an ion beam etching unit using the sample stage is also disclosed.

18 Claims, 5 Drawing Sheets

Figure 1:
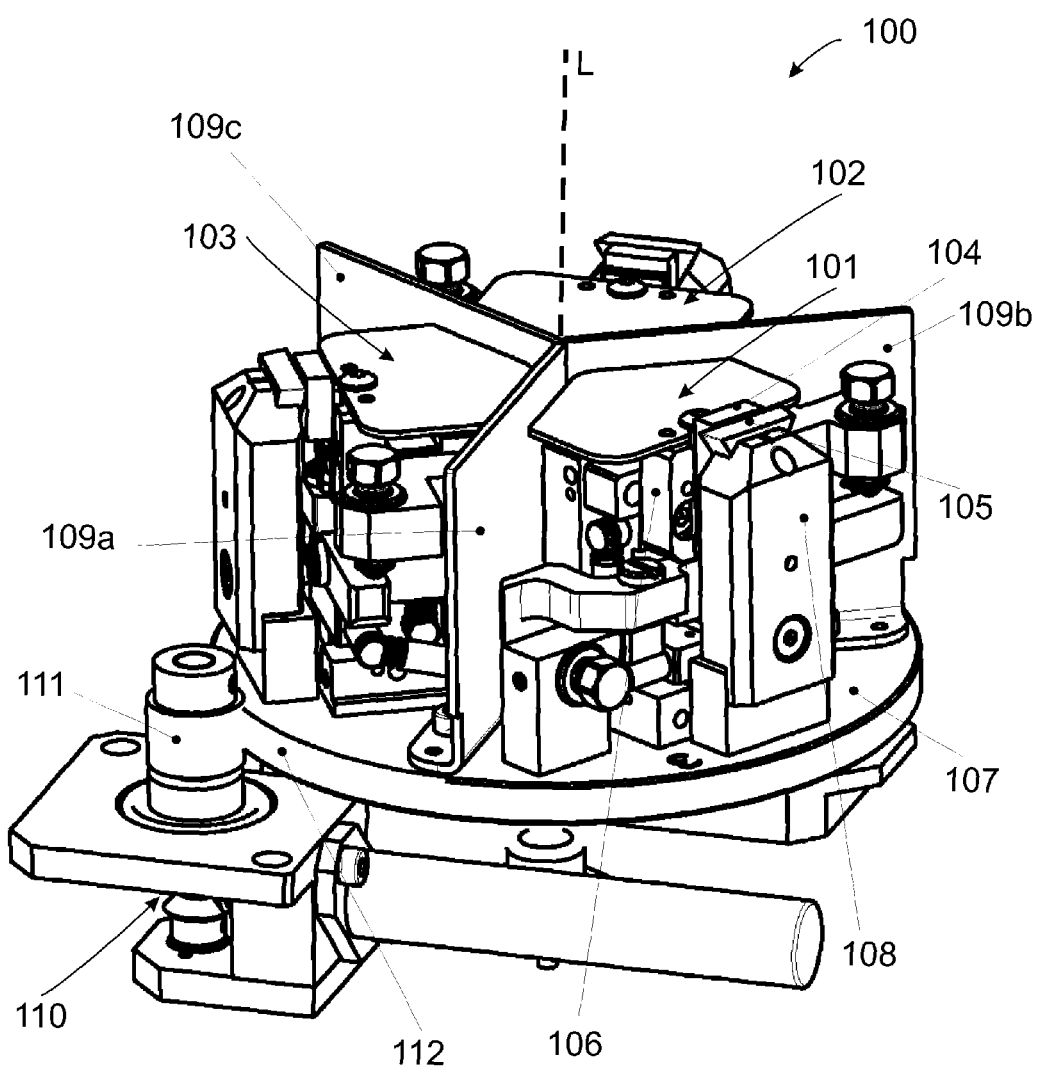

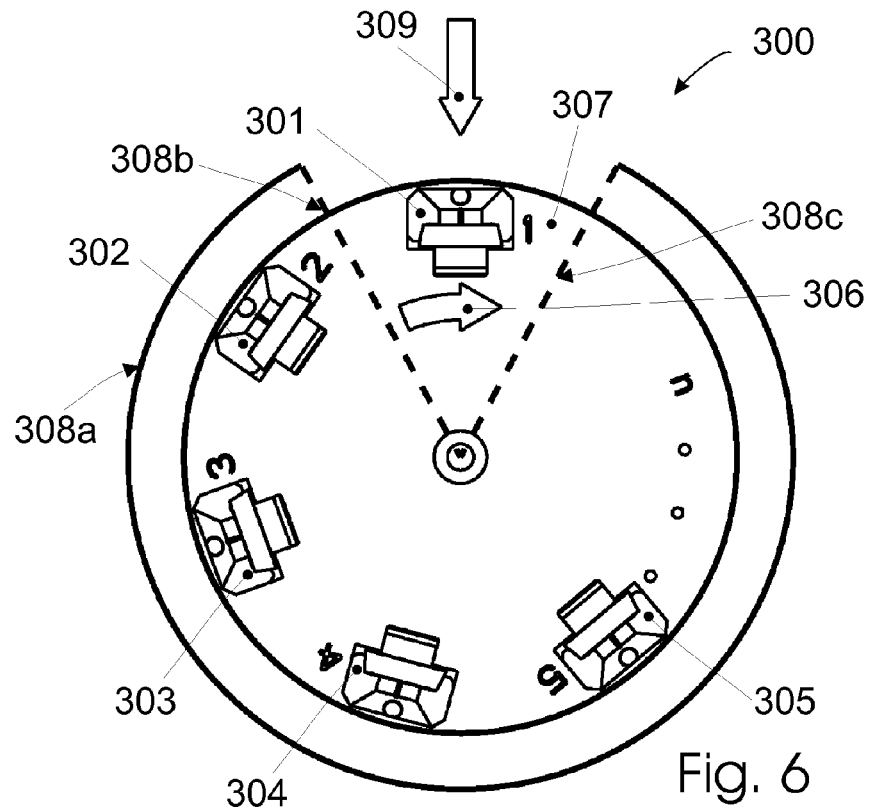
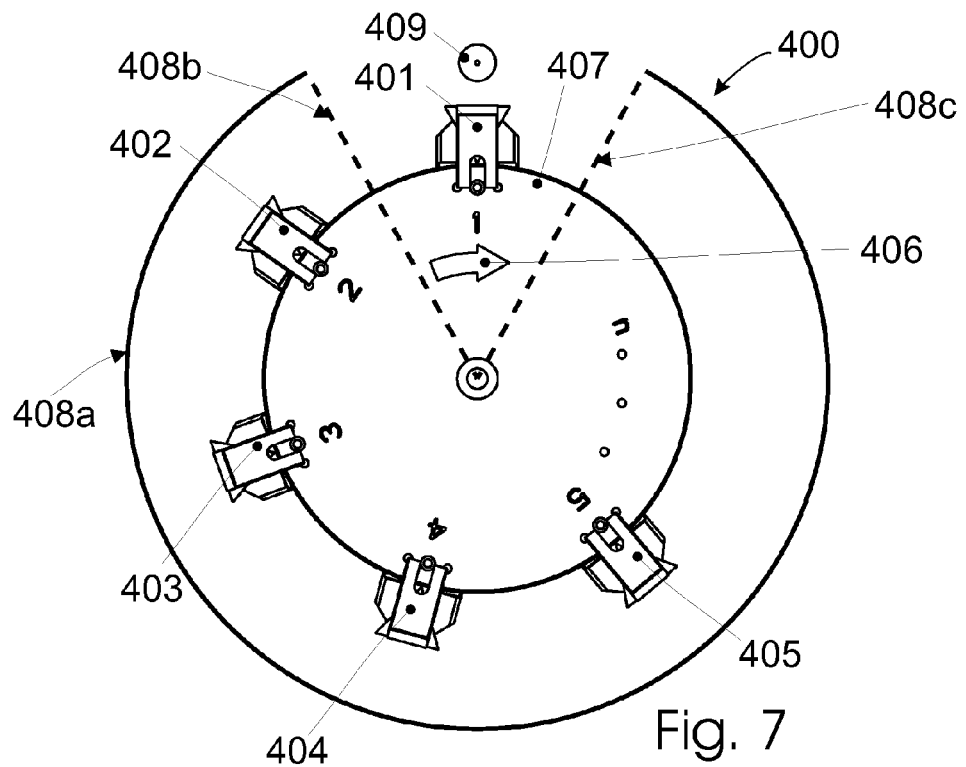

APPARATUS AND METHOD FOR SAMPLE PREPARATION

CROSS REFERENCE TO RELATED APPLICATIONS

This application claims priority of Austrian patent application number A 168/2011 filed Feb. 9, 2011, the entire disclosure of which is incorporated by reference herein.

FIELD OF THE INVENTION

The invention relates to a sample stage for processing a sample in an ion beam etching apparatus, having at least one positioning arrangement that comprises a receiving apparatus and a mask, a sample being mountable in the receiving apparatus with reference to an ion beam that is directed toward the sample stage during an ion beam etching operation, and the sample being positionable in terms of its position relative to the mask.

The invention further relates to a method for sample preparation in an ion beam etching unit.

BACKGROUND OF THE INVENTION

Ion beam etching is a method often utilized to prepare samples whose structure is then typically investigated by scanning electron microscopy (SEM) and transmission electron microscopy (TEM). This technology is used in particular in research, materials research, and quality control for many materials, such as semiconductors, metals, ceramics, plastics, and the like. To carry out the process, the samples are mounted on a sample stage of an ion beam etching unit, and aligned in the beam path of one or more ion beams. Ion beam etching units are typically high-vacuum units that work with a baseline pressure of $10^{-6}$ mbar. The ions most commonly used are argon ions, usually at an acceleration voltage from 1 to 10 kV. The quality of the image resolution in the electron microscope is very substantially dependent, in this context, on the quality of the prepared sample. Among the ion beam etching processes known in practice are, in particular, ion beam slope etching, ion polishing of SEM samples, the wire shadowing method, and ion beam preparation of standard TEM samples. While the last two methods are used for TEM samples, ion beam slope etching is used to prepare cross-sectional SEM samples. In slope etching, profiles of the sample are exposed using the ion beam, a region of the sample being protected, by a mask arranged on the surface of the sample or aligned with respect to the surface of the sample, from material removal by the ion beam. An ion beam slope etching process that has proven particularly effective for producing high-quality SEM samples is one in which at least two ion beams, preferably three ion beams, are guided onto the sample surface at a predefined angle to one another. This method is disclosed in WO 2008/106815 A2.

The ion beam etching units known from the existing art and currently on the market have the disadvantage that a manual sample switchover is necessary after each etching operation. In most cases, a sample switchover requires aeration and opening of the vacuum chamber, as well as re-application of the vacuum. In ion beam etching units that work with an airlock, inward and outward lock transfer is necessary at each sample switchover. These transfer operations also necessitate aeration and deaeration of portions of the unit. Sample switchovers of this kind are time-consuming, and result in low equipment capacity utilization, low sample throughput, and consequently poor cost-effectiveness. It is furthermore impossible to utilize the capacity of such apparatuses over a long period of time (e.g. overnight) without requiring a manual sample switchover by an operator. In addition, as a result of aeration, each sample switchover represents an opportunity for contamination with airborne particles, requiring that the equipment be serviced at shorter time intervals.

German Published Application 2313 096 describes a sample holder for etching thin layers, in which multiple samples are positioned selectably on a turntable into an ion beam.

SUMMARY OF THE INVENTION

It is an object of the invention to eliminate the disadvantages known from the existing art. The intention is in particular to achieve, with the invention, better equipment capacity utilization and thus greater cost-effectiveness, and to minimize the number of sample switchovers.

This object is achieved according to the present invention in that in the context of the sample stage, which is embodied as a switchable stage and comprises at least two positioning arrangements and a mechanism that enables a switchover between positions in which one of the positioning arrangements on the sample stage is respectively orientable toward the ion beam of the ion beam etching apparatus, the sample in the positioning arrangement being exposed to the ion beam while conversely the respectively remaining positioning arrangements face away from the ion beam, the positioning arrangements are arranged in one common vessel, and at least one protective divider is arranged at least between the one respective positioning arrangement that is oriented toward the ion beam of the ion beam etching apparatus and the respectively remaining positioning arrangements that face away from the ion beam.

Thanks to the arrangement according to the present invention in one common vessel, aeration and opening of portions of the unit, e.g. the vacuum chamber, after each completed sample preparation is no longer necessary. That operation can be carried out only after all the samples have been completely prepared by ion beam etching. Because the positioning arrangements are arranged in one common vessel, the samples mounted thereon can be prepared successively with no need to break the vacuum. Non-use times are also significantly decreased, since capacity utilization of the ion beam etching unit over a longer period of time (e.g. overnight) is possible with no need for manual intervention by an operator for sample switchover.

The sample stage is preferably mounted in a flanged housing that can be attached in vacuum-tight fashion onto the vacuum chamber of an ion beam etching unit. By switching the positions of the positioning arrangement, the samples can be exposed preferably sequentially to the ion beam. While one sample is being exposed to the ion beam and prepared (processing position), the respectively remaining samples face away from the ion beam (waiting position). After preparation ends, the prepared sample switches from the processing position into the waiting position, and a sample previously facing away from the ion beam and yet to be prepared switches from the waiting position into the processing position.

Sample preparation by means of ion beam etching occurs preferably sequentially. It is furthermore possible, after a first preparation operation on each sample in a first run, to carry out a second or further preparation run on all or selected samples with no need for a manual sample switchover that includes aeration and opening of portions of the unit. In the context of the processing of heat-sensitive samples, for example, a need often exists for inserting pauses during ion beam etching in order to reduce stress on the sample. Thanks to the invention, heat-sensitive samples can therefore be switched into the waiting position in order to insert the pause, and preparation thereof can then be completed in a second or further preparation run. For certain applications it may be necessary to cool heat-sensitive samples that are in the waiting position. Cooling apparatuses for ion beam etching units are known to one skilled in the art. For certain samples it may also be necessary, subsequently to the ion beam etching operation that is usually carried out with a high-energy ion beam, to process the sample again briefly using a lower-energy ion beam. This processing with a lower-energy ion beam produces a cleaning effect on the previously exposed sample surface. Thanks to the invention, the possibility exists of processing a larger number of samples in any sequence with different preparation parameters.

The sample stage encompasses at least two positioning arrangements, preferably at least three or more positioning arrangements. The greater the number of positioning arrangements that the sample stage comprises, the higher the capacity utilization of the unit. For example, sample stages having up to 10 positioning arrangements are favorable because in this case, despite the high capacity utilization of the ion beam etching unit, the sample stage has manageable dimensions and the necessary maintenance intervals, e.g. for the ion source, can be adhered to. This does not, however, exclude the possibility of the sample stage also having more than 10 positioning arrangements.

In a preferred embodiment, the sample stage encompasses a turntable rotatable about a rotation axis, the positioning arrangements preferably being arranged on the rotatable turntable at identical angular offsets from one another, and the positioning arrangements being preferably sequentially orientable toward the ion beam by rotation of the turntable. Rotation of the turntable thus causes the positioning arrangements, with the samples fastened therein, to be switched respectively into the processing position or the waiting position. This embodiment is particularly compact and moreover has the advantage of accommodating a large number of positioning arrangements on the sample stage in space-saving fashion. In a first sub-variant in the manner of a horizontal turntable or sample carousel, the rotation axis of the turntable is oriented substantially vertically. In a second sub-variant in the manner of a vertical turntable, the rotation axis of the turntable is oriented substantially horizontally.

In another advantageous embodiment of a sample stage according to the present invention, the latter encompasses a movable support of elongated configuration, the positioning arrangements being arranged, preferably at regular intervals, along the length of the elongated support and the positioning arrangements being sequentially orientable toward the ion beam by moving the support in a longitudinal direction.

In a preferred sub-variant, the support is embodied as a slide rail on which the positioning arrangements are fastened.

In order to enable accurate and specific positioning of the respective positioning arrangement with respect to the ion beam, the sample stage comprises a controllable drive system for respectively rotating the turntable or moving the support. A controller controls the drive system in known fashion. The drive system can be arranged outside or inside the vacuum. In a preferred variant, the drive system is a controllable gear drive whose manner of operation is well known to one skilled in the relevant art. For example, for rotation of the turntable a drive gear of the drive system engages into a gear set located on the outer edge of the turntable. For longitudinally directed movement of the support, a drive gear of the drive system engages, for example, into a gear set extending longitudinally along the support. In a further variant, the drive system can engage directly onto the drive shaft of the turntable. It is furthermore also possible to move the turntable by means of a vacuum-compatible toothed belt. Vacuum-compatible toothed belts are known from the existing art.

During the ion beam etching process, material is continuously removed by means of the ion beam from the sample located in the processing position. The risk exists in this context that these material particles may settle onto the samples located in the waiting position and consequently contaminate them, thereby possibly impairing the quality of the samples. It is therefore highly advantageous, in order to protect the positioning arrangements facing away from the ion beam from contamination, that according to the present invention, as mentioned above, protective dividers are arranged between positioning arrangements. With regard to the material nature of the protective divider, it is important that it be produced from a vacuum-compatible material that is easy to clean. Vacuum-compatible materials of this kind are known to one skilled in the relevant art. Because the protective divider is also at least partly exposed to the ion beam during the ion beam etching operation, it should be a material having a very low etching rate in order to minimize erosion. Hard metals, in particular steel, have proven particularly advantageous in practical use.

In a first variant, the protective divider is arranged permanently on the sample stage. Preferably it is welded to the sample stage or joined permanently to the sample stage by being bolted on or using other fastening mechanisms.

In a further variant, the protective divider is arranged positionably. In a first sub-variant of a positionable protective divider, it encompasses a foldable, slidable, or pivotable cover that is openable and closable by means of a spring mechanism. This is to be understood to mean, for example, covers that, as a result of sliding, pivoting, or hinging of the cover, or by compression of the cover in the manner of a bellows, expose an opening and thereby enable a switchover of the positioning arrangements. The spring mechanism can be triggered by movement of the sample stage, for example either by way of a moving positioning arrangement or by means of a lever, with the result that the cover exposes an opening. As soon as the next positioning arrangement has switched into the processing position, the cover closes again by spring force.

In a second variant, the positionable protective divider encompasses a cover that comprises vacuum-compatible overlapping blades or slats extending substantially vertically in the manner of a vertical blind. The slats are movable. Upon a switchover in the positioning of the positioning arrangements, the positioning arrangements can pass through the slats of the cover of the protective divider.

In a third variant, the positionable protective divider encompasses at least one foldable, slidable, or pivotable cover that has its own drive system associated with it for opening and closing. This is to be understood, as in the case of the variant recited above, to mean covers that expose an opening both as a result of sliding, pivoting, or hinging of the cover or by compression of the cover in the manner of a bellows, and thereby enable a switchover of the positioning arrangements. This variant is disadvantageous, as compared with the variant recited above having the spring mechanism, in that greater complexity in terms of control engineering exists here, since the opening and closing of the cover must occur synchronously in time with the switchover of the positioning arrangements.

In an implementation that is easy to achieve, each positioning arrangement is separated by a protective divider from the respectively adjacent positioning arrangements. It is useful in this context to use the variant in which the protective divider is arranged permanently on the sample stage.

A specific embodiment of the sample stage according to the present invention provides for exactly three positioning arrangements that are arranged at an angle of 120° on the turntable, a protective divider arranged perpendicular to the turntable and extending radially with respect to the rotation axis being arranged between each of the three positioning arrangements.

The sample stage according to the present invention is preferably arranged in a flanged housing that is embodied as a vacuum flange. The flanged housing having the sample stage arranged therein is referred to herein as a "sample stage flange." The sample stage flange is flange-mounted onto the vacuum chamber of the ion beam etching unit. The invention therefore also refers to a sample stage flange that encompasses a sample stage according to the present invention as described above.

The invention further encompasses a method for sequential preparation of at least two samples in an ion beam etching unit, in which method the sample stage according to the present invention is utilized.

The method according to the present invention encompasses the following steps:
(a) fastening the samples in the at least two positioning arrangements of a sample stage according to the present invention, manually aligning the samples in the respective positioning arrangements,
(b) arranging the sample stage in the vessel,
(c) orienting one of the positioning arrangements toward the ion beam by moving the sample stage, the sample in the positioning arrangement being exposed to the ion beam, while conversely the respectively remaining positioning arrangements face away from the ion beam, and processing the sample exposed to the ion beam by means of ion beam etching,
(d) switching the positions by moving the sample stage and orienting the next positioning arrangement toward the ion beam and preparing the sample by means of ion beam etching,
(e) repeating steps (c) and (d) until all the samples have been prepared by means of ion beam etching, and
(f) if applicable, repeating steps (c) to (e).

The switching of positions in step (d) preferably occurs sequentially, i.e. the samples are prepared in sequential order.

As is readily apparent from the method steps, all the samples are manually aligned in the respective positioning arrangements (step (a)) before the sample stage is arranged in the vessel, i.e. before the vacuum chamber is closed and a vacuum is applied. The masks preferably have a fixed position in the positioning arrangements. The samples are positioned relative to the respective masks. During the ion beam etching process, the respective aligned sample-mask unit is positioned relative to the ion beam by switching the positions, and the sample can be processed with the ion beam. As already mentioned above, all or selected samples can also be processed repeatedly in two or more runs.

BRIEF DESCRIPTION OF THE DRAWING VIEWS

Figure 2:
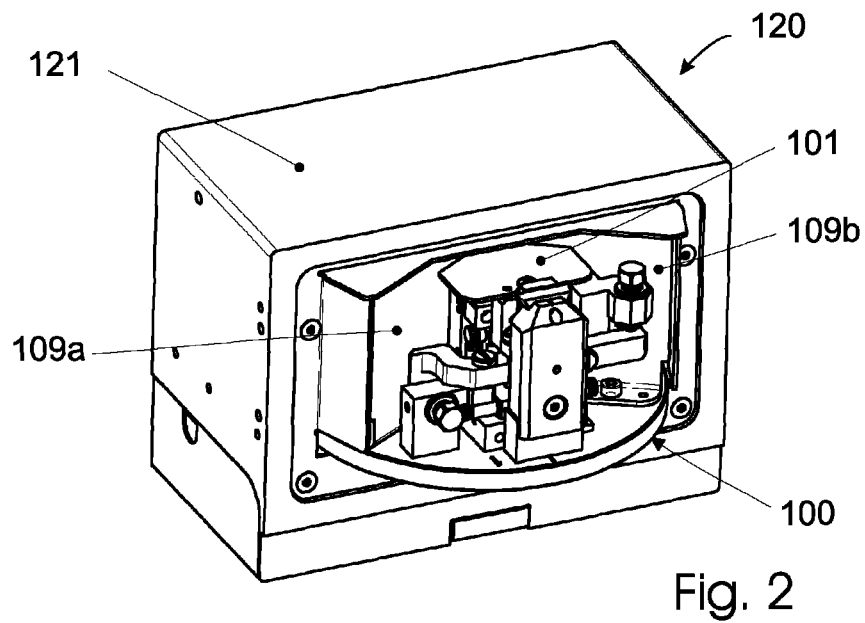
Figure 5:
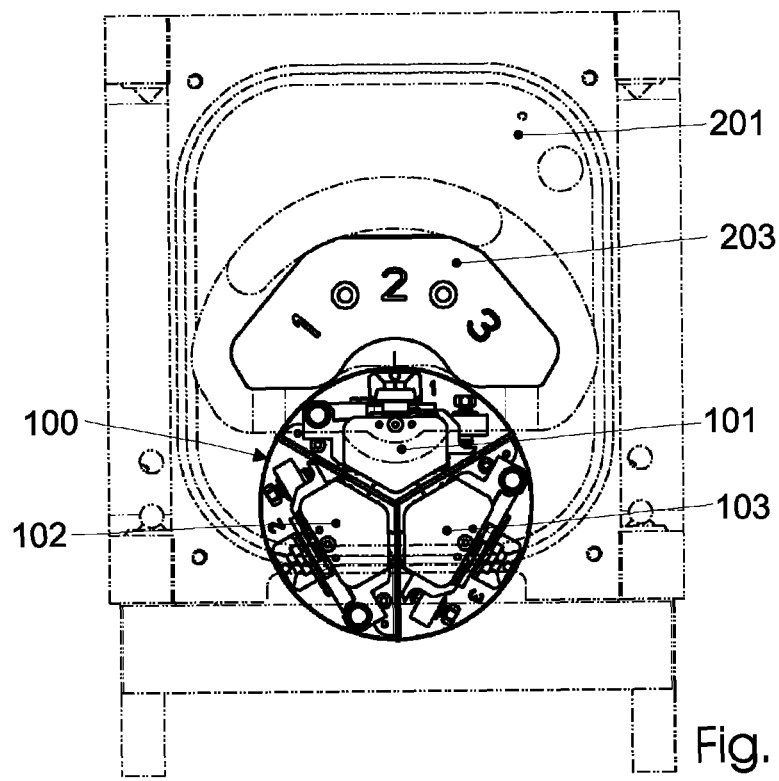
Figure 3:
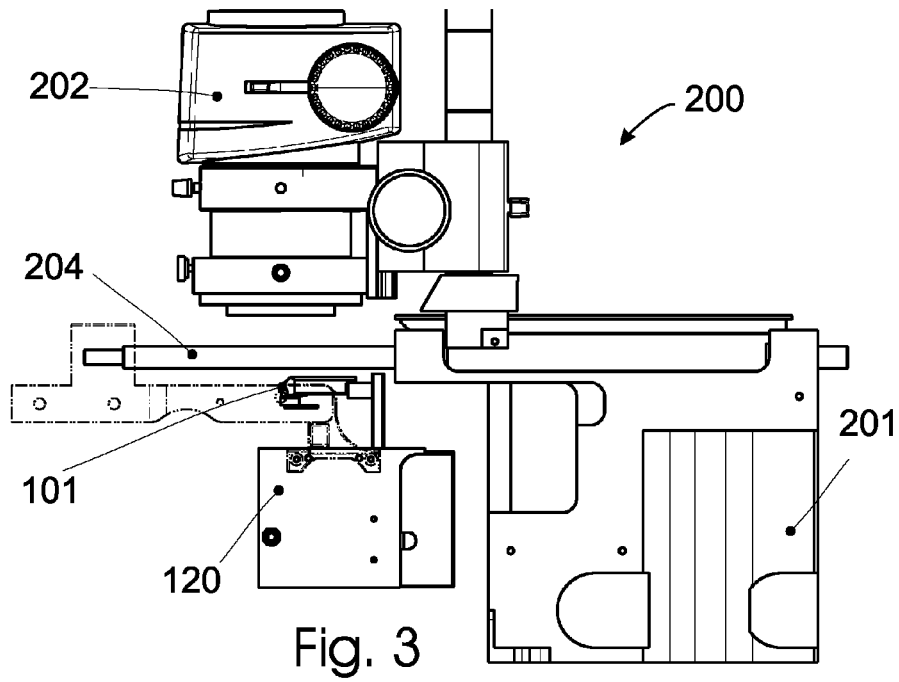
Figure 4:
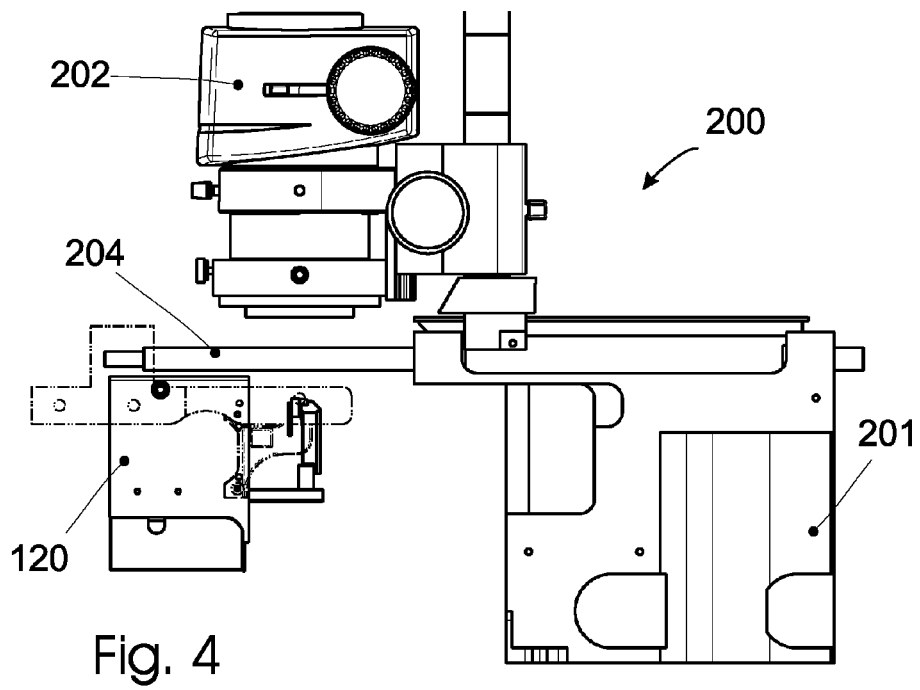
Figure 8:
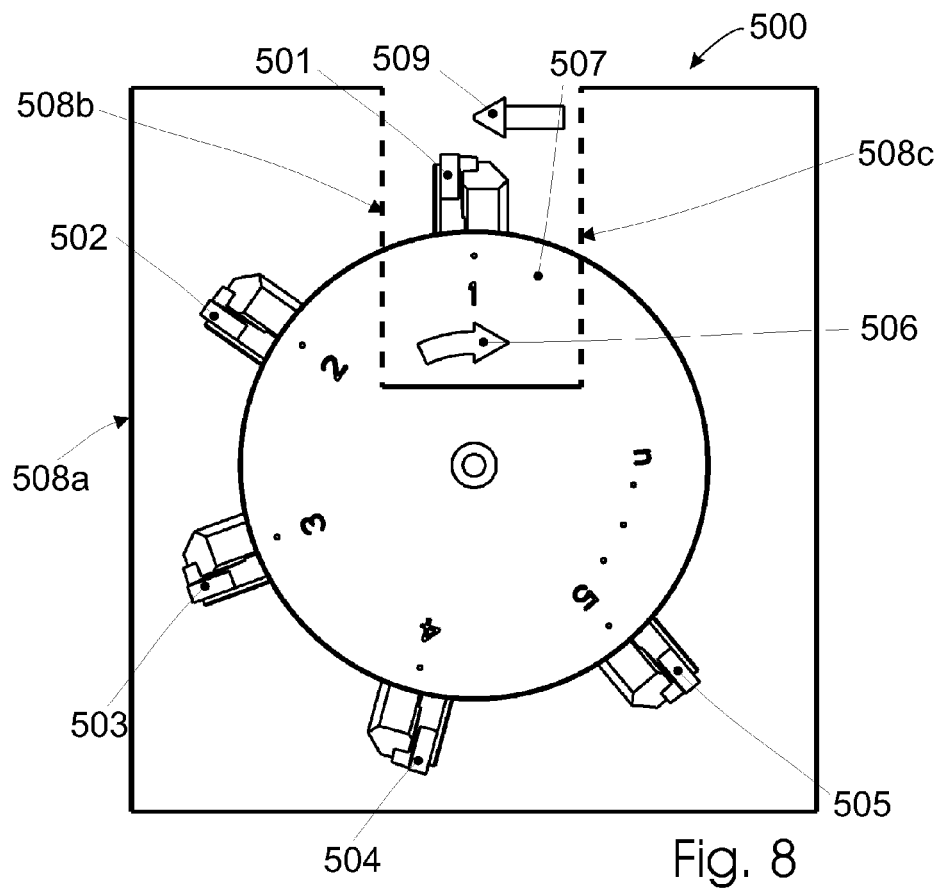
Figure 9:
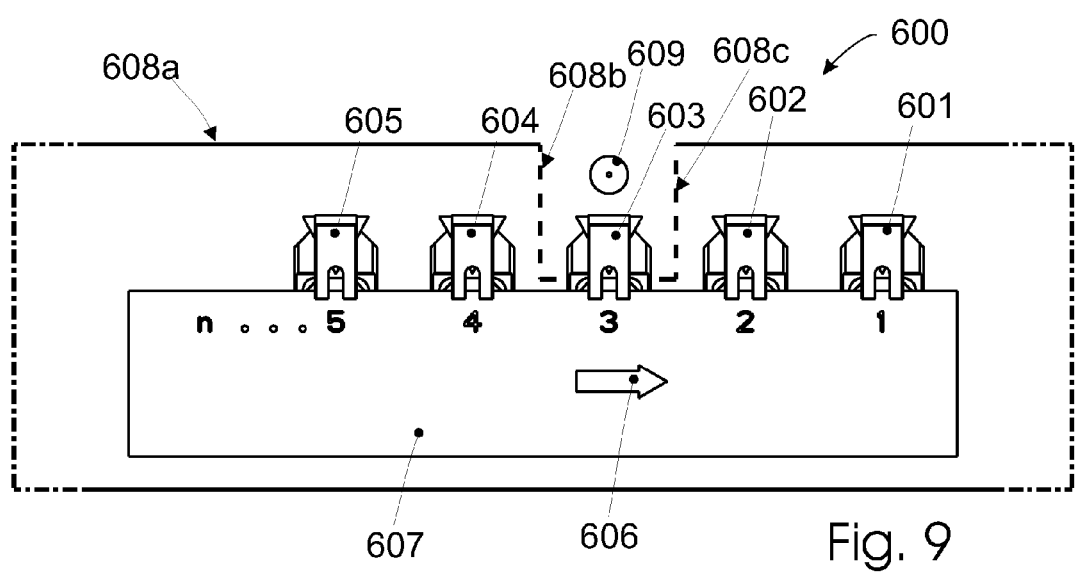

The invention, together with further advantages, is explained below with reference to non-limiting exemplifying embodiments that are depicted in the appended drawings, in which FIG. 1 is a perspective view of a first embodiment of a rotatable sample stage according to the present invention having a vertical rotation axis and having a total of three positioning arrangements, FIG. 2 is a perspective view of a sample stage flange having the sample stage of FIG. 1 arranged therein, FIG. 3 is a side view of an opened ion beam etching unit having the sample stage flange of FIG. 2 mounted therein, in a first alignment position tilted 90°, FIG. 4 shows the ion beam etching unit of FIG. 3, the sample stage flange being pivoted into a second alignment position, FIG. 5 is a section through the closed vacuum chamber of the ion beam etching unit of FIG. 3 and FIG. 4, the sample stage flange being in the operating position, FIG. 6 is a plan view of a second embodiment of a rotatable sample stage according to the present invention, having a vertical rotation axis and a plurality of positioning arrangements, FIG. 7 is a side view of a third embodiment of a rotatable sample stage according to the present invention, having a horizontal rotation axis and a plurality of positioning arrangements, FIG. 8 is a side view of a fourth embodiment of a rotatable sample stage according to the present invention, having a horizontal rotation axis and a plurality of positioning arrangements, and FIG. 9 is a side view of a fifth embodiment of a sample stage according to the present invention in the form of a slide rail.

DETAILED DESCRIPTION OF THE INVENTION

FIG. 1 shows a first embodiment of the invention in the form of a rotatable sample stage 100 for an ion beam etching unit, which stage is mounted rotatably around a vertical rotation axis L (horizontal turntable). The sample stage encompasses a turntable 107 on which a total of three positioning arrangements 101, 102, 103 are arranged at an angular offset of 120° from one another. The configuration of the individual positioning arrangements 101, 102, 103 is known per se to one skilled in the art, and is designed for an ion beam slope etching method as one described in WO 2008/106815 A2. Each positioning arrangement 101, 102, 103 encompasses a receiving apparatus 106, adjustable in two planes, on which a sample 104 can be mounted, as well as a mask holder 108 having a mask 105. Arranged between each of the three positioning arrangements 101, 102, 103 is a protective divider 109*a*, 109*b*, 109*c* in the form of a metal protective panel, arranged perpendicular to turntable 107 and extending radially with respect to the rotation axis. As is more clearly evident from FIGS. 2 and 5, the purpose of protective dividers 109*a*, 109*b*, 109*c* is to prevent positioning arrangements 101, 102, 103 that are in a waiting position from being contaminated with sample material removed during the etching operation. For rotation of sample stage 100, the latter has associated with it a gear drive system 110 in which a drive gear 111 engages into a tooth set (not shown) located on outer edge 112 of the turntable.

FIG. 2 is a perspective view of a sample stage flange 120 having sample stage 100 of FIG. 1 mounted therein. As is clearly evident from FIG. 2, only one of the positioning arrangements 101, 102, 103 is arranged externally and consequently is exposed to the ion beam (processing position), while the respectively remaining positioning arrangements 101, 102, 103 are arranged in flange housing 121 of sample stage flange 120 and are thus in the waiting position. In FIG.

2, positioning arrangement 101 is in the processing position, while positioning arrangements 102, 103 are located inside flange housing 121 in the waiting position. As a result of a rotation of sample stage 100 through an angle of 120°, positioning arrangements 101, 102, 103 switch their positions, i.e. they switch respectively from the waiting position into the processing position and from the processing position into the waiting position, the switchover preferably occurring sequentially. The respective positioning arrangements 101, 102, 103 in the waiting position are protected by the corresponding protective dividers 109a, 109b, 109c from contamination by the removed sample material produced in the context of the etching operation.

FIGS. 3 and 4 are each side views of an opened ion beam etching unit 200 having sample stage flange 120 of FIG. 2 mounted therein. Upon startup of ion beam etching unit 200, sample stage flange 120 is attached in vacuum-tight fashion onto vacuum chamber 201 (vessel) in which the ion sources are arranged (see FIG. 5, which shows a section through a closed vacuum chamber 201 with attached sample stage flange 120). Before application of a vacuum and before the ion beam etching operation begins, the three samples 104 are mounted on positioning arrangements 101, 102, 103 of sample stage 100 and immediately thereafter aligned manually relative to the respective masks 105. Alignment is accomplished on the one hand by precise mounting (adhesive bonding) of sample 104 on the respective receiving apparatus 106, and by means of positioning screws with reference to the fixedly positioned mask 105. Prior alignment of the samples enables preferably sequential ion beam etching of all the samples in one run or, if necessary, of all or selected samples in a second or further run. In FIG. 3, sample stage flange 120 is in a first alignment position tilted 90°. In FIG. 4, sample stage flange 120 is in its second alignment position, this alignment position also representing the position in which sample stage flange 120 is then, by means of a carrier rail 204, displaced horizontally in the direction of vacuum chamber 201 and attached thereto in vacuum-tight fashion. Ion beam etching unit 200 furthermore comprises a binocular 202 for sample alignment.

After loading and alignment of the three samples, sample stage flange 120 is attached to the vessel of ion beam etching unit 200, and the sample chamber is pumped down in order to produce a high vacuum (usually at least $10^{-6}$ mbar). FIG. 5 is a plan view through a section through the closed vacuum chamber 201 with sample stage flange 120 attached, sample stage 100 being emphasized. Positioning arrangement 101 is located in the processing position, while the remaining positioning arrangements 102 and 103 are in the waiting position. The etching process occurs in accordance with the ion beam slope etching process from WO 2008/106815 A2, recited above. In accordance therewith, as described in WO 2008/106815 A2, three ion beams that are integrated into one ion source 203 are guided, at a predefined angle to one another, onto the sample surface of sample 104 of positioning arrangement 101. The samples are prepared sequentially by bringing positioning arrangements 101, 102, 103 into the respective processing and waiting positions by rotation of the sample stage.

FIG. 6 is a plan view of a second embodiment of a rotatable sample stage 300 that, like sample stage 100, is likewise embodied as a carousel-like horizontal turntable having a vertical rotation axis, but that comprises a plurality of positioning arrangements (301, 302, 303, 304, 305 . . . n) offset at identical angles from one another and arranged on a turntable 307. For example, up to ten positioning arrangements can be arranged on turntable 307 ($n \leq 10$), since sample stage 300 in that way, despite high capacity utilization of the ion beam etching unit, has manageable dimensions, and the necessary maintenance intervals, for example for the ion source, can be adhered to. The positioning arrangements of sample stage 300 correspond in principle, in terms of their configuration, to positioning arrangements 101, 102, 103 described above. Positioning arrangement 301 is located in the processing position, while the remaining positioning arrangements are in the waiting position. For rotation of the sample stage 300, the latter likewise has an above-described gear drive system 110 associated with it. Arrow 306 represents the rotation direction of sample stage 300 upon a switchover in positions, and arrow 309 represents the direction of the ion beam that is directed toward the sample mounted in positioning arrangement 301. Turntable 307 having the positioning arrangements is arranged in a protective housing 308a; the positioning arrangement in the processing position (here positioning arrangement 301) is located outside protective housing 308a, exposed to the ion beam, and furthermore shielded from the remaining positioning arrangements by means of two positionable protective covers 308b, 308c (dashed lines) arranged at an angle to one another. Protective covers 308b, 308c can be embodied, as described above in detail, as foldable, pivotable, or slidable covers, for example in the form of swing doors that are openable and closable by means of a spring mechanism or by means of a drive system.

FIG. 7 is a side view of a third embodiment of a rotatable sample stage 400 that is embodied as a turret-like vertical turntable having a horizontal rotation axis. Sample stage 400 comprises a plurality of positioning arrangements (401, 402, 403, 404, 405, . . . n) offset at identical angles from one another and arranged on a turntable 307. For example, up to ten positioning arrangements can be arranged on turntable 407 ($n \leq 10$), since in that way the sample stage, despite high capacity utilization of the ion beam etching unit, has manageable dimensions, and the necessary maintenance intervals, for example for the ion source, can be adhered to. The positioning arrangements of sample stage 400 correspond in principle, in terms of their configuration, to positioning arrangements 101, 102, 103 described above. Positioning arrangement 401 is located in the processing position, while the remaining positioning arrangements are in the waiting position. For rotation of the sample stage 400, the latter likewise has an above-described gear drive system 110 associated with it. Arrow 406 represents the rotation direction of sample stage 400 upon a switchover in positions. The ion beam emerges through exit opening 409 (depicted in plan view) and is directed onto the sample mounted in positioning arrangement 401. The positioning arrangements are arranged on turntable 407 in such a way that the ion beam is directed parallel to the horizontal rotation axis of the turntable and perpendicular to the plane of turntable 407. As described above in FIG. 6, in this embodiment as well turntable 407 having the positioning arrangements is arranged in a protective housing 408a; the positioning arrangement in the processing position (here positioning arrangement 401) is located outside protective housing 408a, exposed to the ion beam, and furthermore shielded from the remaining positioning arrangements by means of two positionable protective covers 408b, 408c (dashed lines) arranged at an angle to one another. Protective covers 408b, 408c can be embodied, as described above in detail, as foldable, pivotable, or slidable covers, for example in the form of swing doors that are openable and closable by means of a spring mechanism or by means of a drive system.

FIG. 8 is a side view of a fourth embodiment of a rotatable sample stage 500 that is embodied as a turret-like vertical turntable having a horizontal rotation axis. The configuration corresponds in principle to that of sample stage 400 (see FIG. 7). Sample stage 500 differs from sample stage 400 in that the positioning arrangements (501, 502, 503, 504, 505, . . . n) are arranged on a turntable 507 in such a way that the ion beam is directed perpendicular to the horizontal rotation axis. For example, up to ten positioning arrangements can be arranged on turntable 507 (n≦10), since in that way the sample stage, despite high capacity utilization of the ion beam etching unit, has manageable dimensions, and the necessary maintenance intervals, for example for the ion source, can be adhered to. Arrow 506 represents the rotation direction of sample stage 500 upon a switchover in positions, and arrow 509 represents the direction of the ion beam that is directed onto the sample mounted in positioning arrangement 501. For rotation of the sample stage 500, the latter likewise has an above-described gear drive system 110 associated with it. In this embodiment as well, turntable 507 having the positioning arrangements is arranged in a protective housing 508a; the positioning arrangement in the processing position (here positioning arrangement 501) is located outside protective housing 508a, exposed to the ion beam, and furthermore shielded from the remaining positioning arrangements by means of two positionable protective covers 508b, 508c (dashed lines) arranged substantially parallel to one another. Protective covers 508b, 508c can be embodied, as described above in detail, as foldable, pivotable, or slidable covers, for example in the form of swing doors that are openable and closable by means of a spring mechanism or by means of a drive system. Protective covers 508b, 508c can also be embodied as vacuum-compatible overlapping blades or slats extending substantially vertically in the manner of a vertical blind.

FIG. 9 is a side view of a fifth embodiment of a sample stage 600. The sample stage encompasses an elongated slide rail 607 displaceable reversibly in a longitudinal direction. Positioning arrangements 601, 602, 603, 604, 605 . . . n) are fastened on slide rail 607 at regular intervals lengthwise, and are sequentially orientable toward the ion beam (depicted as a plan view of exit opening 609 of the ion beam) by movement of the slide rail 607 in a longitudinal direction (arrow 606). For example, up to ten positioning arrangements can be arranged on slide rail 607 (n≦10), since in that way the sample stage, despite high capacity utilization of the ion beam etching unit, has manageable dimensions, and the necessary maintenance intervals, for example for the ion source, can be adhered to. For movement of slide rail 607 in a longitudinal direction, sample stage 600 has an above-described gear drive system 110 associated with it, such that a drive gear engages into a tooth set located on the slide rail. In this embodiment, slide rail 607 having the positioning arrangements is arranged in a protective housing 608a. Protective housing 608a is has larger dimensions in the longitudinal direction than shown in FIG. 9 (indicated by dot-dash lines) in order to enable longitudinal displacement of slide rail 607 in both directions. The positioning arrangement in the processing position (here positioning arrangement 603) is located outside protective housing 608a, exposed to the ion beam, and furthermore shielded from the remaining positioning arrangements by means of two positionable protective covers 608b, 608c (dashed lines) arranged substantially parallel to one another. Protective covers 608b, 608c can be embodied, as described above in detail, as foldable, pivotable, or slidable covers, for example in the form of swing doors that are openable and closable by means of a spring mechanism or by means of a drive system. Protective covers 608b, 608c can also be embodied as vacuum-compatible overlapping blades or slats extending substantially vertically in the manner of a vertical blind.

What is claimed is:

1. A sample stage (100, 300, 400, 500, 600) for processing a sample (104) in an ion beam etching apparatus, the sample stage comprising:
   a switching stage having at least two positioning arrangements (101, 102, 103, 301-305, 401-405, 501-505, 601-605), each positioning arrangement comprising a receiving apparatus (106) and a mask (105), wherein a sample (104) is mountable in the receiving apparatus (106) with reference to an ion beam that is directed toward the sample stage (100, 300, 400, 500, 600) during an ion beam etching operation, and the sample (104) is positionable relative to the mask (105);
   a mechanism (107, 307, 407, 507, 607) operable to switchover between positions in which a selected one of the positioning arrangements (101, 301, 401, 501, 603) is respectively orientated toward the ion beam of the ion beam etching apparatus such that the sample (104) in the selected positioning arrangement (101, 301, 401, 501, 603) is exposed to the ion beam while conversely the remaining non-selected positioning arrangements (102, 103, 302-305, 402-405, 502-505, 601, 602, 604, 605) face away from the ion beam, wherein the positioning arrangements (101, 102, 103, 301-305, 401-405, 501-505, 601-605) are configured to be arranged in one common vessel; and
   at least one protective divider (109a, 109b, 109c; 308b, 308c; 408b, 408c; 508b, 508c; 608b, 608c) arranged at least between the selected positioning arrangement (101, 301, 401, 501, 603) that is oriented toward the ion beam and the remaining non-selected positioning arrangements (102, 103, 302-305, 402-405, 502-505, 601, 602, 604, 605) that face away from the ion beam.

2. The sample stage according to claim 1, wherein the switching stage includes a turntable (107, 307, 407, 507) rotatable about a rotation axis (L), wherein the positioning arrangements are arranged on the rotatable turntable at identical angular offsets from one another about the rotation axis and the positioning arrangements are sequentially orientable toward the ion beam by rotation of the turntable.

3. The sample stage according to claim 2, wherein the rotation axis of the turntable (107, 307) is substantially vertical.

4. The sample stage according to claim 2, wherein the rotation axis of the turntable (407, 507) is substantially horizontal.

5. The sample stage according to claim 1, wherein the switching stage includes a movable support (607) of elongated configuration, wherein the positioning arrangements (601-605) are arranged at regular intervals along the length of the elongated support and the positioning arrangements are preferably sequentially orientable toward the ion beam by moving the support in a longitudinal direction.

6. The sample stage according to claim 5, wherein the support is embodied as a slide rail (607) on which the positioning arrangements are fastened.

7. The sample stage according to claim 2, further comprising a controllable drive system for rotating the turntable.

8. The sample stage according to claim 5, wherein the sample stage comprises a controllable drive system for moving the support.

9. The sample stage according to claim 1, wherein the at least one protective divider (109a, 109b, 109c; 308b, 308c; 408b, 408c; 508b, 508c; 608b, 608c) is arranged to separate each positioning arrangement (101, 102, 103, 301-305, 401-405, 501-505, 601-605) from each other positioning arrangement adjacent thereto.

10. The sample stage according claim 1, wherein the at least one protective divider (109a, 109b, 109c) is arranged permanently.

11. The sample stage according to claim 1, wherein the at least one protective divider (308b, 308c; 408b, 408c; 508b, 508c; 608b, 608c) is arranged positionably.

12. The sample stage according to claim 11, wherein the positionable protective divider (308b, 308c; 408b, 408c; 508b, 508c; 608b, 608c) includes a protective cover that is openable and closable by means of a spring mechanism.

13. The sample stage according to claim 11, wherein the positionable protective divider (508b, 508c; 608b, 608c) includes a protective cover that comprises overlapping slats.

14. The sample stage according to claim 11, wherein the positionable protective divider (308b, 308c; 408b, 408c; 508b, 508c; 608b, 608c) includes a protective cover that is openable and closable by means of a drive system associated with the protective cover.

15. The sample stage according to claim 2, wherein exactly three positioning arrangements (101, 102, 103, 301, 302, 303, 401, 402, 403, 501, 502, 503) are arranged at angular offsets of 120° on the turntable (107, 307, 407, 507), and a respective protective divider (109a, 109b, 109c) is arranged to extend radially relative to the rotation axis (L) between each angularly adjacent pair of the exactly three positioning arrangements (101, 102, 103, 301, 302, 303, 401, 402, 403, 501, 502, 503).

16. A sample stage flange (120), the sample stage flange (120) comprising:
- a flange housing (120); and
- a sample stage arranged at least partially within the flange housing, the sample stage comprising:
  - a switching stage having at least two positioning arrangements, each positioning arrangement comprising a receiving apparatus and a mask, wherein a sample is mountable in the receiving apparatus with reference to an ion beam that is directed toward the sample stage during an ion beam etching operation, and the sample is positionable relative to the mask;
  - a mechanism operable to switchover between positions in which a selected one of the positioning arrangements is respectively orientated toward the ion beam of the ion beam etching apparatus such that the sample in the selected positioning arrangement is exposed to the ion beam while conversely the remaining non-selected positioning arrangements face away from the ion beam, wherein the positioning arrangements are configured to be arranged in one common vessel; and
  - at least one protective divider arranged at least between the selected positioning arrangement that is oriented toward the ion beam and the remaining non-selected positioning arrangements that face away from the ion beam.

17. A method for sequential preparation of at least two samples in an ion beam etching unit, encompassing the steps of:
(a) fastening the samples in the at least two positioning arrangements of a sample stage according to claim 1 and manually aligning the samples in the respective positioning arrangements;
(b) arranging the sample stage in a vessel;
(c) orienting a selected one of the positioning arrangements toward the ion beam by moving the sample stage, the sample in the selected positioning arrangement being exposed to the ion beam, while conversely the remaining non-selected positioning arrangements face away from the ion beam, and processing the sample exposed to the ion beam by means of ion beam etching;
(d) switching positions by moving the sample stage and orienting a next selected positioning arrangement toward the ion beam and preparing the sample in the next selected positioning arrangement by means of ion beam etching; and
(e) repeating steps (c) and (d) until all the samples have been prepared by means of ion beam etching.

18. The method according to claim 17, wherein the step of switching of positions occurs sequentially.

* * * * *